United States Patent [19]
Lindenberg et al.

[11] Patent Number: 5,520,697
[45] Date of Patent: May 28, 1996

[54] APPARATUS FOR CORRECTING THE POSITION OF A STENT

[75] Inventors: Josef Lindenberg; Wolfram Schnepp-Pesch, both of Karlsruhe, Germany

[73] Assignee: Angiomed AG, Karlsruhe, Germany

[21] Appl. No.: 371,580

[22] Filed: Jan. 12, 1995

Related U.S. Application Data

[63] Continuation of Ser. No. 59,964, May 13, 1993, abandoned.

[30] Foreign Application Priority Data

Jun. 20, 1992 [DE] Germany ............ 42 20 295.7

[51] Int. Cl.⁶ .................................................. A61B 19/00
[52] U.S. Cl. ........................................................ 606/108
[58] Field of Search ............................. 606/1, 110, 113, 606/127, 159, 190, 198, 205–211, 108

[56] References Cited

U.S. PATENT DOCUMENTS

| | | | |
|---|---|---|---|
| 3,831,585 | 8/1974 | Brondy et al. | 128/749 |
| 4,467,802 | 8/1984 | Maslanka | 606/206 |
| 4,655,219 | 4/1987 | Petruzzi | 606/206 |
| 4,830,002 | 5/1989 | Semm | 606/207 |
| 4,865,017 | 9/1989 | Shinozuka . | |
| 4,990,151 | 2/1991 | Wallsten | 606/108 |
| 5,011,482 | 4/1991 | Goode et al. | 606/1 |
| 5,053,041 | 10/1991 | Ansari et al. | 606/1 |
| 5,057,114 | 10/1991 | Wittich et al. | 606/127 |
| 5,059,199 | 10/1991 | Okada et al. | 606/127 |
| 5,098,440 | 3/1992 | Millstead | 606/108 |
| 5,108,406 | 4/1992 | Lee | 606/127 |
| 5,201,741 | 4/1993 | Dulebohn | 606/113 |
| 5,224,954 | 7/1993 | Watts et al. | 606/205 |

FOREIGN PATENT DOCUMENTS

| | | |
|---|---|---|
| 0160870 | 4/1985 | European Pat. Off. . |
| 0169784 | 7/1985 | European Pat. Off. . |
| 0408245 | 7/1990 | European Pat. Off. . |
| 3607933 | 9/1986 | Germany .......... 606/194 |
| 4025799 | 8/1990 | Germany . |
| 4115136 | 11/1992 | Germany . |
| 62-14811 | 4/1987 | Japan . |
| 2149212 | 12/1990 | Japan . |
| 1002076 | 10/1963 | United Kingdom . |
| 2020557 | 5/1979 | United Kingdom . |

OTHER PUBLICATIONS

Patent Abstracts of Japan, vol. 14, No. 100 (C–693)(4043) 23 Feb., 1990 and JP–A–13 08 553 (Sumitomo Electric) 13 Dec., 1989 *Abstract*.

Toy–Smoot Laparoscopic Hernioplasty–Toy et al. Surgical Laparoscopy and Endoscopy vol. 1, No. 3 pp. 151–155–1991.

*Primary Examiner*—Stephen C. Pellegrino
*Assistant Examiner*—Glenn Dawson
*Attorney, Agent, or Firm*—Antonelli, Terry, Stout & Kraus

[57] ABSTRACT

An apparatus for correcting a positioning of a stent for widening or keeping open a stenosis, in blood vessels, the urethra, the ureter, etc. The apparatus includes a guide part slidably housing an elongated wire part provided at a forward end thereof with radially expandable wire portions having structures for grasping the stent.

9 Claims, 2 Drawing Sheets

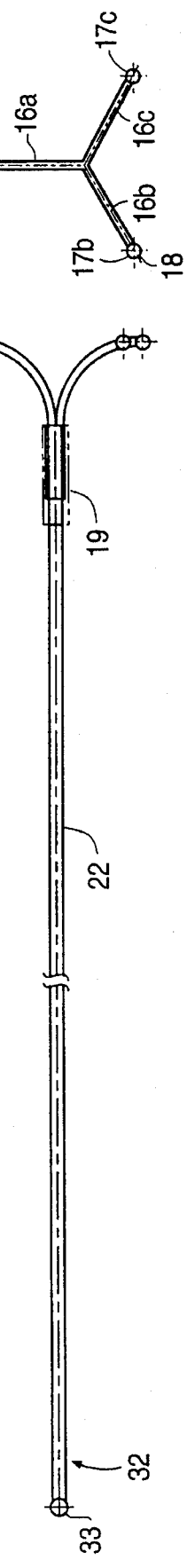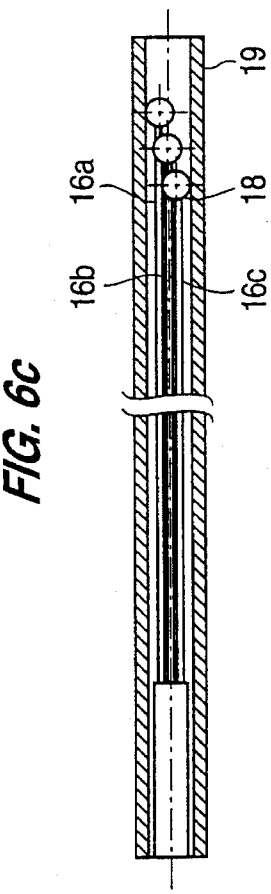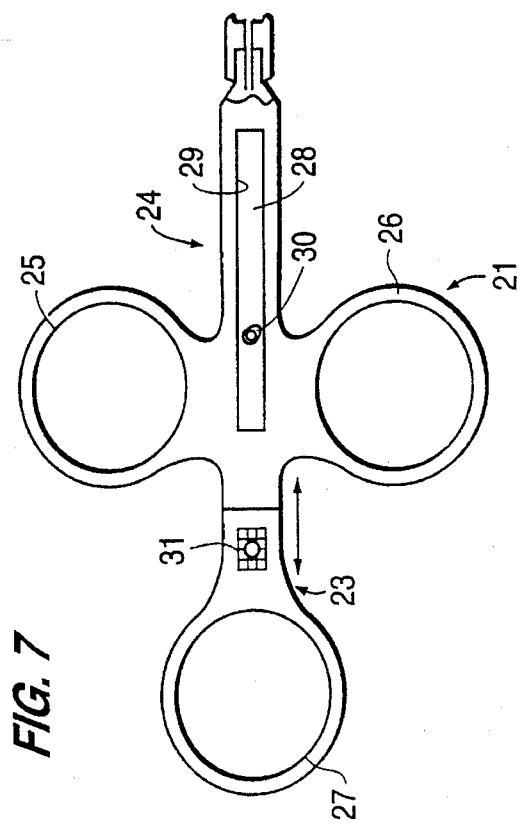

APPARATUS FOR CORRECTING THE POSITION OF A STENT

This application is a continuation of Ser. No. 08/059,964, filed May 13, 1993, now abandoned.

FIELD OF THE INVENTION

The invention relates to an apparatus for correcting the position of a stent in a vessel or the like, such as a stent for widening a stenosis or the like, with at least one guide part.

BACKGROUND OF THE INVENTION

For keeping open stenoses or the like in blood vessels or similar hollow members in the human body, such as the ureter, urethra or the like, use is made of short stents, which are inserted in the vicinity of the stenosis and are intended to support the sane as a result of the intrinsic stability. Preferably wire stents are used, which are either widened by means of a balloon catheter in the radially expanded position or in the case of construction from a memory alloy material following insertion widened due to the body heat to an automatically radially prestamped, widened position. It can occur that such a stent is not positioned in the desired manner. It can also occur that the stent moves for same reason despite the widening. If e.g. a stent enters the urethra in the vicinity of the urethral sphincter, it can no longer fulfil its function and this can lead to incontinence. In such a case it is desirable to either reapply the stent if the original position is not desired, or subsequently correct the axial position of the stent in the body vessel. The seine applies with respect to stents in other organs, such as biliary or fenoral stents.

SUMMARY OF THE INVENTION

The aim underlying the invention is to provide an apparatus allowing the correction of the position of such a stent.

According to the invention, in an apparatus of the aforementioned type by providing an elongated wire part provided at its front end with radially expandable wire portions.

The elongated wire part provided with the radially expandable wire portions is inserted through a guide part, such as a cystoscope, which can optionally have a second working channel, a catheter, a tubular part, a hollow stylet or the like, in blood vessels, the urethra or the like, into the vicinity of the stent and namely to just in front of the stent if the latter is to be further advanced or behind the stent if the latter is to be retracted, or solely into the area covered by the stent. This is followed by the radial widening of the radially widenable wire portions, either in that they are prestamped in such a way that they automatically radially expand after passing out of the guide part when the latter has been retracted, or in that the radially widenable wire portions can be widened by a suitable device, such as a pull wire, until their furthest radially outwardly projecting areas can engage in front of or behind the stent or on the latter in the central region thereof. As a result of the advance or retraction of the wire part the stent position can be modified.

According to a preferred development the wire portions are of a self-expanding nature on being relieved and in particular the wire portions are constructed in one piece with the elongated wire part. In such a case the wire portion preferably comprises individual interlinked wire strands, which divide in the vicinity of the expandable wire portions, but are recombined at the front free end thereof. The wire portions have a prestamping such that they can radially expand on freeing from externally acting forces. In an alternative construction the wire part has a pull wire guided through a hollow wire and which at the front of the wire portions engages thereon, whereas at the rear end connection takes place to the front end of the hollow wire, the wire portions also being constructed in one piece with the hollow wire. In such a construction the expansion of the expandable wire portions can be brought about by pulling on the pull wire.

In order to allow a better action of the radially widenable wire portions on the stent, according to further preferred developments the radially expandable wire portions are provided in their furthest radially outwardly projecting area with corners and/or the radially expandable wire portions are provided on their furthest radially outwardly projecting areas with hooks. Alternatively the radially expandable wire portions are provided with thickened portions on their furthest outwardly projecting areas and in particular the thickened portions are small balls.

Whilst the guide tube can basically be constructed as a metal tube, it can be provided at its front end with flat edges and can therefore be constructed as a hollow stylet. Optionally it is introduced percutaneously with the aid of an internal stylet. The guide part can also be flexible, e.g. in the form of a catheter.

Whilst the radially expandable wire portions basically form a small basket, they can also have a helical construction and here again the helix can in cross-section or in projection not merely be given a circular, oval or elliptical cross-section, but can also be angular in projection.

According to a highly preferred development of the invention, the radially expandable wire portions are fixed to the elongated wire portion (2) and in particular the expandable wire portions are soldered in the elongated wire portion. Whereas the radially expandable wire portions can be made from steel, such as spring steel and can be held in their reciprocally engaging insertion position by a guide tube or hose, whereby they radially expand from the guide tube or hose during advance as a result of their pretension, so that the radially expandable wire portions move into their radially expanded position in the relieved state, according to a preferred development the radially expandable wire portions are made from a nickel-titanium alloy (Nitinol). The use of such a material also permits what has been described hereinbefore. According to a preferred further development tile radially expandable wire portions are oriented in axially parallel manner in a low temperature position and extend radially further outwards in a high temperature position.

Whilst the wire portions can fundamentally form a basket-like structure, being guided and interconnected by the front end thereof and radially expand in intermediate areas, according to a highly preferred development, in the radially outwardly directed position radially furthest outward projecting areas of the radially expandable wire portions are the free ends thereof and in particular in the expanded position of the radially expandable wire portions the furthest radially outwardly extending areas are approximately perpendicular to the axis of symmetry of the apparatus. To avoid any injury risk in this case, a preferred development is characterized in that the free ends are provided with blunted or rounded portions, e.g. in the form of spherical ends. To require a minimum amount of radial space particularly in the insertion position, in which the wire portions are very closely juxtaposed in a guide tube or hose and consequently permit the use of thin guide tubes or hoses, an extremely preferred development provides for the radially expandable wire portions to have different lengths. The ends, particularly if they are provided with small balls or the like, are then not located in a common radial plane in the insertion position, so that the balls are not close together and are instead axially displaced, so that the balls are also located in radially succeeding manner on the different radially expandable wire ends.

BRIEF DESCRIPTION OF THE DRAWINGS

Further advantages and features of the invention can be gathered from the claims and the following description of embodiments with reference to the attached drawings, wherein:

FIGS. 6a–c A further preferred development of the apparatus according to the invention, in which in the radially expanded functional state the free ends of the expandable wire portions extend furthest radially outwards and terminate in directions which are substantially perpendicular to the axis of the elongated wire part, the free ends being provided with rounded balls (FIGS. 6a, 6c) and have different lengths (FIG. 6c).

FIG. 7 An actuator for an apparatus according to the invention according to one of the above-described embodiments.

DETAILED DESCRIPTION

Figure 1:
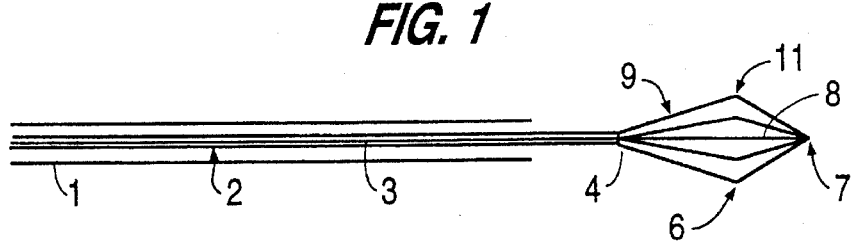
FIG. 1 A first embodiment of the apparatus for correcting the position of a stent with a pull wire in accordance with the invention.
Figure 2:
FIG. 2 A variant of the apparatus according to the invention for correcting the position of a stent with a hollow stylet as the guide tube.
Figure 3:
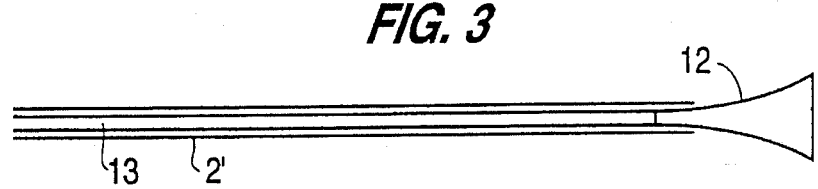
FIG. 3 Further elements which may be used in an apparatus according to the invention for correcting the position of a stent, with a guide tube on the stent to be fitted, as well as a slide for sliding the seine out of the guide tube.

The apparatus according to the invention for correcting the position of a stent fitted in a vessel or the like firstly has a guide part 1 in the form of a guide tube or hose or a styler (FIG. 2). The apparatus according to the invention also has an elongated wire part 2, which in the embodiment of FIG. 1 has a hollow wire element 3, e.g. formed from helically wound wire, whose individual turns engage on one another. To the front end 4 of the hollow wire 3 is either fixed a basket 6 on the hollow wire part or individual wires of the hollow wire 3 are not coiled and instead are guided in a longitudinal plane to the front end 7 of the complete wire part 2. At the latter they are connected to the front end of a pull wire 8, which is guided through the hollow wire part 3 up to its rear end and out of the latter (not shown). The wire portions 9 of the basket 6 can have prestamped corners or edges 11. Without loading the wire portions 9 engage closely on one another, so that the complete wire part 2 can be moved through the guide part 1. If the basket 6 with the wire portions 9 is located in the vicinity of a fitted stent 12, it can be expanded into the radially expanded or widened position shown in FIG. 1 by pulling on the pull wire 8. The corners 11 then engage, as after axial positioning, either in front of or behind the stent 12 or in the interior thereof, e.g. its meshes or turns. As a result of the movement of the wire part 2 the stent 12 can be moved axially backwards and forwards and better positioned in an appropriate manner.

The guide part 1 is constructed as a hollow stylet in FIG. 2. This e.g. makes it possible to percutaneously correct the position of a stent, such as e.g. in the case of a biliary or fenoral stent. The hollow stylet in FIG. 2 can also be inserted in an apparatus constructed according to FIG. 1, whereas the guide part of FIG. 1, either in the form of a tube or a hose, can also be used in the construction according to FIG. 2, as will be described hereinafter.

In the case of the construction according to FIG. 2 the elongated wire part can be a single wire or a helical or spiral wire, optionally formed from several individual strands, which then in turn form a small basket 6, which can be separately fitted to the wire part 2. In FIG. 2 the wire portions 9 of the basket 6 are pretensioned or prestamped in the radially expanded position shown, so that without the effect of external forces the basket 6 is expanded into said radially widened position. The individual wires 9 are interconnected at the front free ends 7 of the basket 6. If the basket 6 is drawn into the guide part 1, it is radially compressed by the latter. There is firstly an introduction of the guide part 1 into the vicinity of the stent whose position is to be corrected. The wire part 2 with the radially compressed basket 6 located in the guide part 1 is then further advanced, so that the basket 6 is freed and can radially expand into the position shown in FIG. 2. Following axial position its edges 11 once again engage upstream, downstream or in the vicinity of the stent 12, so that the position of the latter can be corrected by pushing or pulling on the wire part 2.

Further elements of the apparatus according to the invention can be, in addition to the stent 12, a guide part 2', which can correspond to the guide part 2 and a slide 13, which can be slid through the guide part 2' and can slide the stent located therein out of the guide part 2'. If a correction of the axial position of the stent 12 is still necessary, then following the removal of the slide 13, a wire part 2 according to FIGS. 1 or 2 can be inserted through the guide part 2', until it can act on the fitted stent 12 in order to position the latter.

Figure 4A:
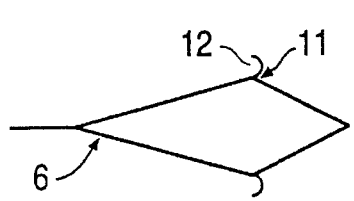
FIGS. 4a–4c Developments of elements provided or constructed on expandable wire portions for engaging on the stent in the form of hooks additionally provided on the expandable wire portion, or hooks constructed on the wire portions, or spherical widened portions provided on the expandable wire portions.
Figure 4B:
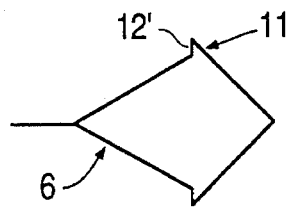
Figure 4C:
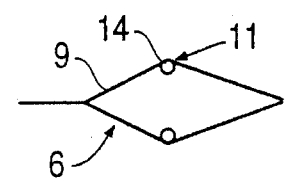

Whereas in FIGS. 1 and 2 the wire portions 9 of the basket 6 are only provided with corners or edges 11, in the vicinity thereof it is also possible to provide small hooks 12, as shown in FIG. 4a. The corners or edges 11 can also be shaped to hooks 12', as is the case in FIG. 4b. As means for acting on the stent 12 or engaging in its turns or meshes, in the vicinity of the corners it is also possible to provide widened portions on the wire parts 9, e.g. in the form of small balls 14 as shown in FIG. 4c.

Figure 5A:
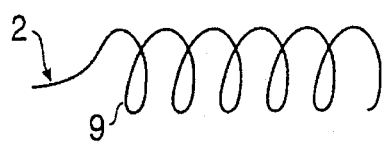
FIGS. 5a–5b Further developments of the expandable wire portions of an inventive apparatus with a helix with circular turns and a helix with multiangular turns.
Figure 5B:
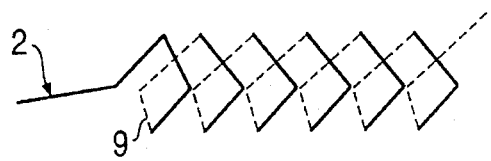

FIG. 5 shows another variant of the radially expandable wire portions 9' or 9" in the form of spirals with a helical contour. Whereas the outer contour in the case of the wire portion 9 is cylinder envelope-like, i.e. it has a circular cross-section or a circular axial projection, which can also be e.g. elliptical or oval, the spiral wire portion 9" of FIG. 5b has several corners or edges 11 and e.g. as a result a rectangular or multiangular cross-section or corresponding axial projection. Such constructions are in particular provided if the wire portions 9' or 9" are to act in the vicinity of the stent 12, i.e. not upstream or downstream thereof. Here again the corners 11 engage in the meshes of the stent 12, so that the latter can be positioned in optimum manner by pushing or pulling. The edges 11 can be constructed in accordance with FIGS. 4a to 4c.

FIGS. 6a to 6c show another construction according to the invention, in which the radially expandable, distal wire portions 16a, 16b, 16c can be made from a nickel-titanium alloy such as Nitinol and have a shape memory. The elongated wire part 22 can also be made from a corresponding alloy, but no shape memory contour is impressed thereon.

To avoid injury the expandable, distal wire portions 16a–16c are provided with small balls 18 at their free ends 17a–17c. The desired blunting or rounding of the free ends 17a–17c can also be obtained in same other way.

In the low temperature position, such as at 0° C., the free wire portions 16a–16c extend parallel to one another, as shown in FIG. 6c. As can be gathered from FIGS. 6a–6c, they have different lengths, so that the balls 18 of the individual wire portions 16a–16c are in different axial positions in the low temperature setting thereof and are not radially juxtaposed, so that the internal diameter of the insertion catheter or tube 19 can be smaller than would be the case if the three balls 18 were located in one radial plane.

In the high temperature setting of tile nickel-titanium material of the expandable wire portions 16a–16c, which must be reached under 35° C., the transition temperature generally being between 10° and 30° C., the expandable, distal wire portions 16a–16c extend arcuately radially outwards, their free ends 17a–17c forming an angle of approximately 90° to the axis of the elongated wire part 22, as can be clearly gathered from FIG. 6a.

For correcting the stent the apparatus according to the invention is inserted with the guide tube 19 and the elongated wire part 22 located therein with expandable wire portions 16a–16c into the vicinity of the previously inserted stent or intraluminal tube. The elongated wire part 22 is advanced until the expandable wire portions 16a–16c pass out of the insertion tube or hose 19 and radially expand in the position shown in FIGS. 6a and 6b, either under a pretension which has existed from the outset, or due to their high temperature setting in this form. The free ends 17a–17c with the balls 18 engage in gaps of the stent or the intraluminal tube, which can be formed from wire and can in particular be knitted, or can comprise flat material provided with openings, so that by advancing and retracting the elongated wire part 22, the axial position of the stent or intraluminal tube can be corrected.

For advancing the elongated wire part 22 in the guide tube or hose 19 there is preferably an actuator, as shown in FIG. 7. The actuator 21 comprises two handle parts 23, 24, which are axially movable relative to one another. The handle part 24 has two gripping rings 25, 26, in which can be placed the index and middle finger, whilst the handle part 23 has a ring part 27 in which is placed the thumb. The guide catheter or tube 19 is fixed to the handle part 24. An axial shoulder 28 of the handle part 23 projects into the handle part 24 and is axially movable to a limited extent therein through a slot guide 29 therein and a can 30 on the axial part 28.

The elongated wire part 22 is fixed on the handle part 23, e.g. by means of a plugging part provided with spring legs 31, the latter embracing a ball 33 fitted to the rear end 32 of the elongated wire pact 22 and which has a larger diameter than the elongated wire part 22. In this way the elongated wire part 22 and with it the expandable wire portions 16a–16c are securely held in the handle part 23. FIG. 7 shows the advanced operating position of the apparatus according to the invention, in which the expandable wire portions 16a–16c project out of the hose or tube 19 (FIGS. 6a and 6b). In the inserted position the handle part 24 and handle part 23 are axially drawn apart and namely until the can 30 strikes against the rear (left) end of the guide slot 29 of the handle part 24. In this insertion position the expandable wire portions 16a– 16c are in the position shown in FIG. 6 within the guide tube or hose 19.

Whereas the construction of the actuator 21 according to FIG. 7 has been explained with reference to an apparatus constructed according to FIGS. 6a–6c, the actuator can also be used in an apparatus according to the invention constructed in accordance with the earlier drawings, the guide part 1 being fixed to the handle part 24 and the wire part 22 to the handle part 23.

We claim:

1. An apparatus for correcting a position of a stent in a vessel, such as a stent for widening a stenosis, said apparatus comprising at least one hollow guide part, and an elongated wire part provided at a front end thereof with radially expandable wire portions having free ends, said elongated wire part with radially expandable wire portions being movable in said hollow guide part, and said radially expandable wire portions having different lengths and, when said radially expandable wire portions are advanced out of said guide part so that distal portions thereof including said free ends are released by said guide part, said distal portions move into a radially expanded position in which said distal portions extend radially outwardly from said elongated wire part approximately perpendicular to an axis of symmetry of the elongated wire part, and wherein said radially expandable wire portions are provided on their free ends with thickened portions.

2. Apparatus according to claim 1, wherein upon release, said distal portions of the wire portions are self-expanding wire portions so as to move into said expanded position.

3. Apparatus according to claim 2, wherein the radially expandable wire portion are constructed in one piece with the elongated wire part.

4. Apparatus according to claim 1, wherein the radially expandable wire portions are fixed to the elongated wire part.

5. Apparatus according to claim 4, wherein the radially expandable wire portions are soldered to the elongated wire part.

6. Apparatus according to claim 1, wherein the radially expandable wire portions are made from a nickel-titanium alloy.

7. Apparatus according to claim 6, wherein the radially expandable wire portions are oriented in a substantially axially parallel manner in a low temperature position and said distal portions thereof including said free ends extend radially further outwards to said expanded position in a high temperature position when released by said guide part.

8. Apparatus according to claim 1, wherein the thickened portions are small ball shaped members.

9. Apparatus according to claim 1, wherein said at least one guide part is flexible.

* * * * *